United States Patent [19]

Midorikawa et al.

[11] Patent Number: 6,080,882
[45] Date of Patent: Jun. 27, 2000

[54] PROCESS FOR PRODUCING ACRYLONITRILE OR METHACRYLONITRILE FROM PROPANE OR ISOBUTANE BY AMMOXIDATION

[75] Inventors: Hideo Midorikawa; Naoki Sugiyama; Hidenori Hinago, all of Kurashiki, Japan

[73] Assignee: Asahi Kasei Kogyo Kabushiki Kaisha, Osaka, Japan

[21] Appl. No.: 09/115,195

[22] Filed: Jul. 15, 1998

[30] Foreign Application Priority Data

Jul. 16, 1997 [JP] Japan .................................. 9-205531
Nov. 18, 1997 [JP] Japan .................................. 9-316805

[51] Int. Cl.[7] .............................................. C07C 253/00
[52] U.S. Cl. ................................................... 558/319
[58] Field of Search ...................................... 558/319

[56] References Cited

U.S. PATENT DOCUMENTS

| | | | |
|---|---|---|---|
| 3,833,638 | 9/1974 | Knox et al. | 558/319 |
| 4,814,478 | 3/1989 | Glaeser et al. | 558/319 |
| 5,049,692 | 9/1991 | Hatano et al. | 558/319 |
| 5,281,745 | 1/1994 | Ushikubo et al. | 558/319 |
| 5,332,855 | 7/1994 | Blanchard et al. | 558/319 |
| 5,334,743 | 8/1994 | Blanchard et al. | 558/319 |
| 5,336,804 | 8/1994 | Blanchard et al. | 558/319 |
| 5,422,328 | 6/1995 | Ushikubo et al. | 502/312 |
| 5,534,650 | 7/1996 | Ushikubo et al. | 558/319 |

FOREIGN PATENT DOCUMENTS

| | | |
|---|---|---|
| 0 767 164 A1 | 4/1997 | European Pat. Off. . |
| 2608768 | 1/1990 | Japan . |
| 5-208136 | 8/1993 | Japan . |
| 2506602 | 3/1994 | Japan . |
| 2599677 | 5/1994 | Japan . |
| 6-92355 | 5/1994 | Japan . |
| 6-285372 | 10/1994 | Japan . |
| 8-225506 | 9/1996 | Japan . |
| 9-157241 | 6/1997 | Japan . |
| 10-57813 | 3/1998 | Japan . |
| 1304665 | 1/1973 | United Kingdom . |

*Primary Examiner*—Johann Richter
*Assistant Examiner*—Joseph Murray
*Attorney, Agent, or Firm*—Pennie & Edmonds LLP

[57] ABSTRACT

Process for producing acrylonitrile or methacrylonitrile from propane or isobutane by ammoxidation at a temperature in the range of from 380 to 500° C. in a fluidized-bed reactor containing a catalyst composition preheated to a temperature of not lower than 300° C. and lower than the ammoxidation reaction temperature, the catalyst composition comprising a carrier having supported thereon an oxide catalyst comprising a compound oxide of molybdenum, vanadium, niobium and at least one element selected from tellurium and antimony, wherein the ammoxidation of propane or isobutane is preceded by a specific temperature elevation operation in which the catalyst temperature in the reactor is elevated, while supplying into the fluidized-bed reactor a molecular oxygen-containing gas together with a combustible gas capable of combustion by reaction with the molecular oxygen in the presence of said catalyst composition, until the temperature of the catalyst composition reaches said ammoxidation reaction temperature. The process of the present invention is advantageous in that the temperature elevation of the catalyst can be performed without suffering a deterioration of the catalytic activity during the temperature elevation, thereby allowing the catalyst to fully exhibit its performance.

4 Claims, 1 Drawing Sheet

PROCESS FOR PRODUCING ACRYLONITRILE OR METHACRYLONITRILE FROM PROPANE OR ISOBUTANE BY AMMOXIDATION

BACKGROUND OF THE INVENTION

1. Field of the Invention

The present invention relates to a process for producing acrylonitrile or methacrylonitrile from propane or isobutane by ammoxidation. More particularly, the present invention is concerned with a process for producing acrylonitrile or methacrylonitrile from propane or isobutane by ammoxidation at a temperature in the range of from 380 to 500° C. (ammoxidation reaction temperature) in a fluidized-bed reactor containing a catalyst composition preheated to a temperature of not lower than 300° C. and lower than the ammoxidation reaction temperature, the catalyst composition comprising a carrier having supported thereon an oxide catalyst comprising a compound oxide of molybdenum, vanadium, niobium and at least one element selected from the group consisting of tellurium and antimony, wherein the ammoxidation of propane or isobutane at the ammoxidation reaction temperature is preceded by a specific temperature elevation operation in which the temperature of the preheated catalyst composition in the fluidized-bed reactor is elevated, while supplying into the fluidized-bed reactor a molecular oxygen-containing gas together with a combustible gas capable of combustion by reaction with the molecular oxygen in the presence of the catalyst composition, until the temperature of the catalyst composition reaches the ammoxidation reaction temperature. By virtue of the above-mentioned specific temperature elevation operation using both a molecular oxygen-containing gas and a combustible gas when the temperature of the catalyst composition is 300° C. or higher, the process of the present invention is advantageous in that the temperature elevation of a catalyst comprising a compound oxide of molybdenum, vanadium, niobium and at least one element selected from tellurium and antimony can be performed without suffering a deterioration of the catalytic activity during the temperature elevation of the catalyst, thereby allowing the catalyst to fully exhibit its inherent performance.

2. Prior Art

It has been well known to produce an unsaturated nitrile, such as acrylonitrile or methacrylonitrile, by ammoxidation of an olefin, such as propylene or isobutene, namely, by reacting an olefin with ammonia and molecular oxygen.

On the other hand, from the viewpoint of reducing the cost for raw materials, attention has been attracted to a process for producing an unsaturated nitrile (such as acrylonitrile or methacrylonitrile) from an alkane (such as propane and isobutane), which is available at low cost as compared to an alkene, by ammoxidation in the presence of a catalyst, i.e., by reacting an alkane with ammonia and molecular oxygen in the presence of a catalyst. Further, a number of proposals have also been made with respect to catalysts for use in the ammoxidation of an alkane.

For example, as a catalyst for use in producing acrylonitrile by ammoxidation of propane, there is known an oxide catalyst containing molybdenum, vanadium, tellurium and niobium. Such a catalyst and a method for producing the catalyst are disclosed in each of Japanese Patent Publication No. 2608768 (published in 1997)(corresponding to U.S. Pat. No. 5,049,692), Unexamined Japanese Patent Application Laid-Open Specification No. 5-208136 (corresponding to U.S. Pat. No. 5,281,745) and Unexamined Japanese Patent Application Laid-Open Specification No. 6-285372 (corresponding to U.S. Pat. No. 5,422,328). Further, Unexamined Japanese Patent Application Laid-Open Specification No. 9-157241 (corresponding to European Patent No. 767,164) discloses an oxide catalyst containing molybdenum, vanadium, antimony and niobium as a catalyst for use in producing acrylonitrile by ammoxidation of propane. These prior art documents have a description concerning ammoxidation reaction conditions employed in the evaluation of the performance of such catalyst. However, with respect to the manner of elevating the temperature of the catalyst before starting the ammoxidation reaction of propane, no description is found in these prior art documents.

Unexamined Japanese Patent Application Laid-Open Specification No. 10-57813 discloses a process for producing acrylic acid by oxidation of propane, using a catalyst containing molybdenum, vanadium and at least one element selected from tellurium and antimony. In this process, the catalyst is subjected to heat treatment virtually in the absence of molecular oxygen, and then subjected to further heat treatment under a stream of air. However, in this prior art document, there is no description as to whether or not such a manner of heat treatment in that process is effective for the ammoxidation reaction of propane or isobutane.

Unexamined Japanese Patent Application Laid-Open Specification No. 8-225506 (corresponding to U.S. Pat. No. 5,534,650) discloses a method for performing an ammoxidation reaction of an alkane in which gaseous ammonia is fed into a reactor from a plurality of ammonia inlets provided therein. However, with respect to the manner of elevating the temperature of a catalyst before starting the ammoxidation reaction of an alkane, no description is found in this prior art document.

Japanese Patent Publication No. 2599677 (published in 1997)(corresponding to U.S. Pat. No. 5,332,855) discloses an ammoxidation method for a saturated hydrocarbon, using a catalyst which contains vanadium, antimony and at least one element selected from iron, gallium and indium; Examined Japanese Patent Application Publication No. 6-92355 (corresponding to U.S. Pat. No. 5,334,743) discloses an ammoxidation method for a saturated hydrocarbon, using a catalyst which contains molybdenum, vanadium and at least one element selected from manganese, zinc, cobalt, copper, lithium, sodium, potassium and silver; and Japanese Patent Publication No. 2506602 (published in 1996)(corresponding to U.S. Pat. No. 5,336,804) discloses an ammoxidation method for a saturated hydrocarbon, using a catalyst which contains vanadium, antimony and bismuth. In these prior art documents, there is a description about an evaluation method for the ammoxidation reaction, in which the temperature of a catalyst contained in a reactor is first elevated to 150° C. while purging the air in the reactor with helium, and then feedstock gases and diluent gases, i.e., propane, ammonia, oxygen, steam and helium, are fed while further elevating the temperature of the catalyst to a predetermined temperature, for example, 300° C., whereupon the catalyst temperature is maintained at the predetermined temperature for 30 minutes, followed by analysis of a gaseous mixture withdrawn from the outlet of the reactor. The present inventors conducted experiments in which the catalysts described in these prior art documents were produced and ammoxidation reactions were conducted using the produced catalysts individually to make various evaluations. As a result, it was found that the performance of the catalyst is almost not affected by the type of gas which is supplied into a reactor containing the catalyst during the elevation of the temperature of the catalyst before starting the ammoxidation reaction. More specifically, the catalyst exhibits the same performance irrespective of whether the gas used during the temperature elevation is air alone or air plus combustible gas selected from feedstock gases.

As a method for the ammoxidation of an olefin by using a catalyst which contains antimony and uranium, British Patent No. 1,304,665 discloses a method in which a catalyst bed comprising a regeneration zone and a reaction zone located adjacent to each other is provided, and molecular oxygen necessary for the ammoxidation is flowed through the regeneration zone of the catalyst bed, together with ammonia in an amount of 3% or more of the whole amount of ammonia to be fed. In this method, the feeding of ammonia to the regeneration zone is intended to suppress a loss of propylene in the regeneration zone. In this prior art document, there is no description as to the manner of elevating the temperature of the catalyst bed before the start of the ammoxidation reaction of propylene.

U.S. Pat. No. 4,814,478 discloses a method in which the ammoxidation reaction of a saturated hydrocarbon is performed using a mixed catalyst of a catalyst comprised mainly of vanadium and antimony and a catalyst comprised mainly of molybdenum, bismuth and iron. In this prior art document, as a specific example of the reaction method, a method using a fixed-bed reactor is described, wherein gaseous raw materials are preheated by means of a "preheat leg", and the resultant preheated gaseous raw materials are then introduced into a catalyst bed. However, this prior art document has no description as to the manner of elevating the temperature of the catalyst bed before starting the ammoxidation reaction.

U.S. Pat. No. 3,833,638 discloses a catalyst for use in the ammoxidation reaction of a saturated hydrocarbon. The catalyst contains molybdenum, cerium and at least one element selected from the group consisting of bismuth and tellurium. In this prior art document, it is described that gaseous raw materials can be fed to the reactor either before or after the internal temperature of the reactor reaches a desired reaction temperature. In this connection, it is noted that the catalyst of this prior art document is of a type such that the regeneration of the catalyst can be performed through contact with air at high temperatures. Therefore, with respect to the technique of this prior art document, it is preferred that the elevation of the internal temperature of the reactor toward a desired reaction temperature is performed while supplying air into the reactor, and the feeding of gaseous raw materials is started after the internal temperature of the reactor has reached the desired reaction temperature.

As described hereinabove, various proposals have been made to provide an improved process for producing an unsaturated nitrile by ammoxidation of an alkane (such as propane and isobutane) in the presence of a catalyst. However, such proposals have been disadvantageous in that the catalytic activity of the specific catalyst (comprising a carrier having supported thereon an oxide catalyst comprised of a compound oxide of molybdenum, vanadium, niobium and at least one element selected from the group consisting of tellurium and antimony) cannot be maintained at a high level when the ammoxidation reaction is performed. Therefore, it has been desired to develop an improved process for producing an unsaturated nitrile from an alkane by ammoxidation, which can maintain the catalytic activity of the catalyst at a high level even after the temperature of the catalyst is elevated to the ammoxidation reaction temperature.

SUMMARY OF THE INVENTION

In this situation, the present inventors have conducted extensive and intensive studies with a view toward developing an improved process for producing an unsaturated nitrile from an alkane by ammoxidation, which can provide a satisfactorily high catalytic activity. As a result, it has unexpectedly been found that, in a process for producing acrylonitrile or methacrylonitrile from propane or isobutane by ammoxidation at a temperature in the range of from 380 to 500° C. (ammoxidation reaction temperature) in a fluidized-bed reactor containing a catalyst composition preheated to a temperature of not lower than 300° C. and lower than the ammoxidation reaction temperature, the catalyst composition comprising a carrier having supported thereon an oxide catalyst comprising a compound oxide of molybdenum, vanadium, niobium and at least one element selected from the group consisting of tellurium and antimony, it is very effective for attaining the above objective to precede the ammoxidation of propane or isobutane at the ammoxidation reaction temperature by a specific temperature elevation operation in which the temperature of the catalyst composition in the fluidized-bed reactor is elevated, while supplying into the fluidized-bed reactor a molecular oxygen-containing gas together with a combustible gas capable of combustion by reaction with the molecular oxygen in the presence of the catalyst composition, until the temperature of the catalyst composition reaches the ammoxidation reaction temperature. The present invention has been completed, based on the above novel finding.

It is, therefore, a primary object of the present invention to provide an improved process for producing acrylonitrile or methacrylonitrile from propane or isobutane by ammoxidation in a fluidized-bed reactor containing a catalyst composition comprising a carrier having supported thereon a catalyst comprised of a compound oxide of molybdenum, vanadium and niobium as well as tellurium and/or antimony, in which the temperature of the catalyst composition can be elevated toward a predetermined ammoxidation reaction temperature using an oxygen-containing gas, such as air, without suffering a deterioration of the catalytic activity of the catalyst.

The foregoing and other objects, features and advantages of the present invention will be apparent from the following detailed description taken in connection with the accompanying drawing and the appended claims.

Description of Reference Numerals

Figure 1:
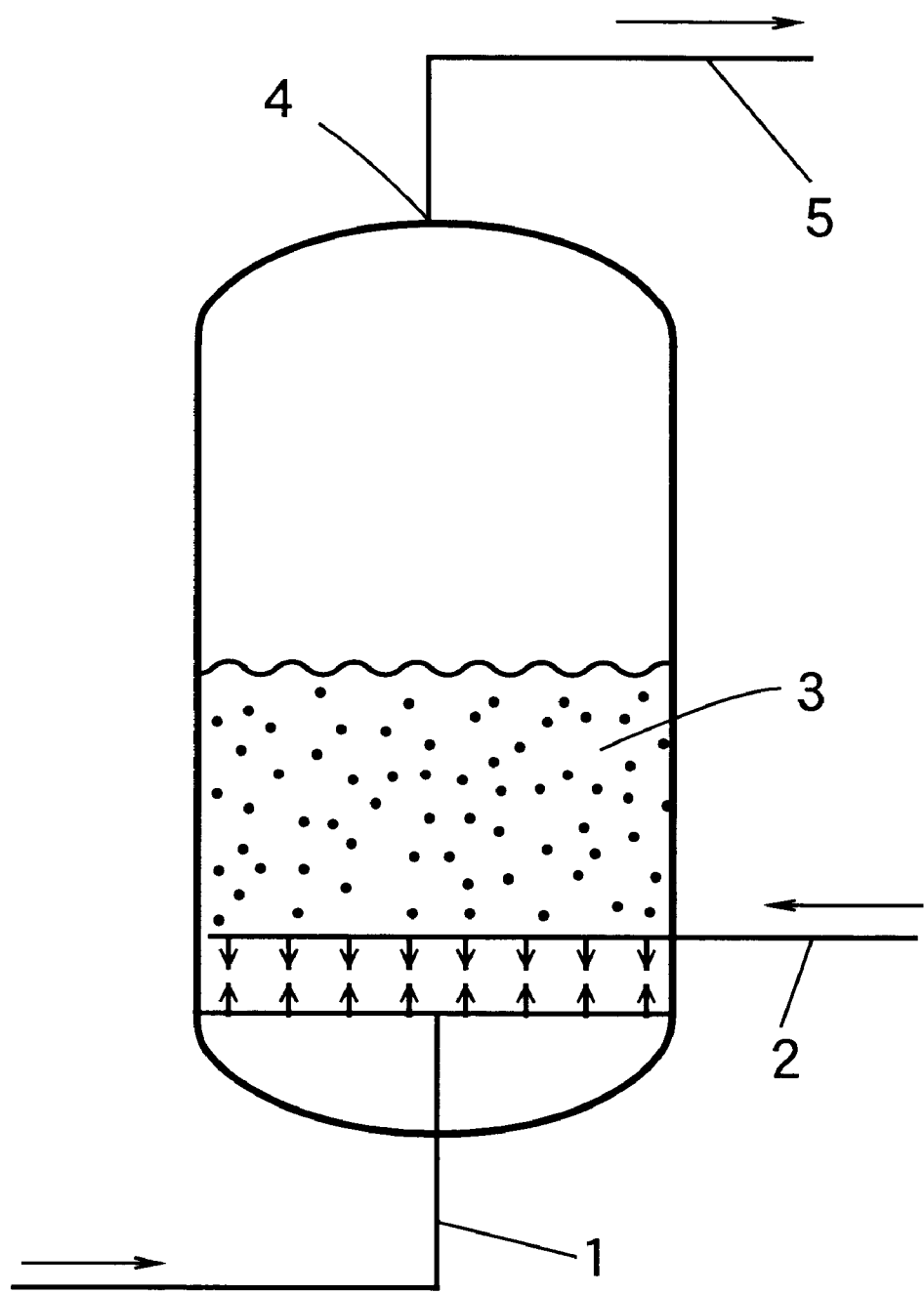
FIG. 1 is a diagrammatic view showing an example of a fluidized-bed reactor suitably employable when the process of the present invention is practiced for commercial-scale production of acrylonitrile or methacrylonitrile.

1: Line for introducing air
2: Line for introducing ammonia and/or propane
3: Fluidized catalyst bed
4: Outlet for the produced gas
5: Line for the effluent

DETAILED DESCRIPTION OF THE INVENTION

In the present invention, there is provided a process for producing acrylonitrile or methacrylonitrile from propane or isobutane by ammoxidation at a temperature in the range of from 380 to 500° C. (ammoxidation reaction temperature) in a fluidized-bed reactor containing a catalyst composition comprising a carrier having supported thereon an oxide catalyst, the oxide catalyst comprising a compound oxide of molybdenum, vanadium, niobium and at least one element selected from the group consisting of tellurium and antimony, the process comprising:
(1) providing a fluidized-bed reactor containing the catalyst composition preheated to a temperature of not lower than 300° C. and lower than the ammoxidation reaction temperature;
(2) elevating the temperature of the preheated catalyst composition in the fluidized-bed reactor, while supplying into the fluidized-bed reactor a molecular oxygen-containing gas together with a combustible gas capable of combustion by reaction with the molecular oxygen in the presence of the catalyst composition, until the temperature of the catalyst composition reaches the ammoxidation reaction temperature; and
(3) changing the supply of the combustible gas and the molecular oxygen-containing gas into the fluidized-bed reactor to a feeding of propane or isobutane, ammonia and molecular oxygen into the fluidized-bed reactor when the temperature of the catalyst composition reaches the ammoxidation reaction temperature, to thereby effect an ammoxidation reaction of the propane or isobutane, thus producing acrylonitrile or methacrylonitrile.

For an easy understanding of the present invention, the essential features and various preferred embodiments of the present invention are enumerated below.

1. A process for producing acrylonitrile or methacrylonitrile from propane or isobutane by ammoxidation at a temperature in the range of from 350 to 550° C. (ammoxidation reaction temperature) in a fluidized-bed reactor containing a catalyst composition comprising a carrier having supported thereon an oxide catalyst, the oxide catalyst comprising a compound oxide of molybdenum, vanadium, niobium and at least one element selected from the group consisting of tellurium and antimony, the process comprising:
(1) providing a fluidized-bed reactor containing the catalyst composition preheated to a temperature of not lower than 300° C. and lower than the ammoxidation reaction temperature;
(2) elevating the temperature of the preheated catalyst composition in the fluidized-bed reactor, while supplying into the fluidized-bed reactor a molecular oxygen-containing gas together with a combustible gas capable of combustion by reaction with the molecular oxygen in the presence of the catalyst composition, until the temperature of the catalyst composition reaches the ammoxidation reaction temperature; and
(3) changing the supply of the combustible gas and the molecular oxygen-containing gas into the fluidized-bed reactor to a feeding of propane or isobutane, ammonia and molecular oxygen into the fluidized-bed reactor when the temperature of the catalyst composition reaches the ammoxidation reaction temperature, to thereby effect an ammoxidation reaction of the propane or isobutane, thus producing acrylonitrile or methacrylonitrile.

2. The process according to item 1 above, wherein the combustible gas is at least one compound selected from the group consisting of $C_1$–$C_8$ alkanes, $C_2$–$C_8$ alkenes, $C_2$–$C_4$ alkynes, $C_4$–$C_5$ dienes, $C_3$–$C_8$ cycloalkanes, $C_4$–$C_8$ cycloalkenes, $C_6$–$C_9$ aromatic hydrocarbons, $C_1$–$C_8$ alcohols, $C_2$–$C_7$ ethers, $C_1$–$C_3$ aldehydes, $C_2$–$C_3$ epoxides, $C_2$–$C_8$ ketones, $C_1$–$C_4$ nitriles, $C_1$–$C_4$ carboxylic acids, $C_2$–$C_5$ esters, $C_1$–$C_6$ nitrogen-containing organic compounds, $C_1$–$C_4$ sulfur-containing organic compounds, hydrogen, ammonia, carbon monoxide, hydrogen sulfide and carbon disulfide.

3. The process according to item 1 above, wherein the combustible gas is at least one compound selected from the group consisting of propane, isobutane, propylene, isobutene, methanol, ethanol, propanol, hydrogen, ammonia and carbon monoxide.

4. The process according to item 1 above, wherein the combustible gas is ammonia.

5. The process according to any one of items 1 to 4 above, wherein the catalyst composition is obtained by a method comprising:

providing a catalyst composition precursor comprising silica and compounds of molybdenum, vanadium, niobium and at least one element selected from the group consisting of tellurium and antimony, and calcining the catalyst composition precursor in an atmosphere of inert gas which is substantially free of molecular oxygen, to thereby obtain a catalyst composition comprising a silica carrier having supported thereon an oxide catalyst, the carrier being present in an amount of from 10 to 70% by weight, based on the total weight of the silica and the oxide catalyst, the oxide catalyst comprising a compound oxide being represented by the following formula (1):

$$Mo_{1.0}V_aNb_bA_cO_x \qquad (1)$$

wherein:
A is at least one element selected from the group consisting of tellurium and antimony; and a, b, c and x are, respectively, the atomic ratios of vanadium, niobium, A and oxygen, relative to the molybdenum, wherein
a is a number from 0.01 to 1.0;
b is a number from 0.01 to 1.0;
c is a number from 0.01 to 1.0;
and
x is a number determined by the valence requirements of the other elements present.

Hereinbelow, the present invention will be described in more detail.

During the temperature elevation of a catalyst composition contained in a fluidized-bed reactor until the temperature reaches an ammoxidation reaction temperature, for uniformly heating the catalyst composition, it is necessary to keep the catalyst composition in a fluidized state by supplying gas, such as air, into the fluidized-bed reactor. The catalyst composition used in the process of the present invention contains an oxide catalyst comprising a compound oxide of molybdenum, vanadium, niobium and at least one element selected from the group consisting of tellurium and antimony. It has been found that, when the catalyst composition used in the process of the present invention is contacted with a molecular oxygen-containing gas, such as air, during the course of the temperature elevation of the catalyst composition to the ammoxidation reaction temperature, a change occurs in the catalyst structure as determined by an X-ray diffraction measurement, causing a deterioration of the catalytic activity of the catalyst, so that problems arise, such as a lowering of the conversion of propane and isobutane and a lowering of the yield of acrylonitrile or methacrylonitrile.

However, the present inventors have unexpectedly found that the deterioration of the catalyst composition, which is likely to occur by contact of the catalyst composition with a molecular oxygen-containing gas during the temperature elevation of the catalyst composition, can be prevented by (1) providing a fluidizedbed reactor containing the catalyst composition preheated to a temperature of not lower than 300° C. and lower than the ammoxidation reaction temperature, and (2) performing a specific temperature elevation operation in which the temperature of the preheated catalyst composition in the fluidized-bed reactor is elevated, while supplying into the fluidized-bed reactor a molecular oxygen-containing gas together with a combustible gas capable of combustion by reaction with the molecular oxygen in the presence of the catalyst composition, until the temperature of the catalyst composition reaches the ammoxidation reaction temperature.

Combustible gases used in the present invention mean gases which can combust when it is reacted with molecular oxygen at 300° C. or higher in the presence of the catalyst composition used in the process of the present invention.

Examples of combustible gases used in the process of the present invention include organic compounds, such as $C_1$–$C_8$ alkanes (e.g., methane, ethane, propane, n-butane, isobutane, pentane, hexane, heptane and octane), $C_2$–$C_8$ alkenes (e.g., ethylene, propylene, n-butene, isobutene, pentene, hexene, heptene and octene), $C_2$–$C_4$ alkynes (e.g., acetylene, methylacetylene and dimethylacetylene), $C_4$–$C_5$ dienes (e.g., butadiene and isoprene), $C_3$–$C_8$ cycloalkanes (e.g., cyclopropane, cyclobutane, cyclopentane, cyclohexane, cycloheptane and cyclooctane), $C_3$-$C_8$ cycloalkenes (e.g., cyclopropene, cyclobutene, cyclopentene, cyclohexene, cycloheptene and cyclooctene), $C_6$–$C_9$ aromatic hydrocarbons (e.g., benzene, toluene, xylene, ethylbenzene, propylbenzene and styrene), $C_1$–$C_8$ alcohols (e.g., methanol, ethanol, propanol, butanol, pentanol, hexanol, heptanol and octanol), $C_2$–$C_7$ ethers (e.g., dimethyl ether, diethyl ether, anisol, tetrahydrofuran, furan and dioxane), $C_1$–$C_4$ aldehydes (e.g., formaldehyde, acetaldehyde, propionaldehyde and valeraldehyde), $C_2$–$C_3$ epoxides (e.g., ethylene oxide and propylene oxide), $C_2$–$C_8$ ketones (e.g., acetone, methyl ethyl ketone, diethyl ketone and methyl benzyl ketone), $C_1$–$C_4$ nitriles (e.g., hydrogen cyanide, acetonitrile, propionitrile, acrylonitrile, methacrylonitrile and isobutyronitrile), $C_1$–$C_4$ carboxylic acids (e.g., formic acid, acetic acid, propionic acid and valeric acid), $C_2$–$C_6$ esters (e.g., methyl formate, ethyl formate, methyl acetate, ethyl acetate, methyl propionate, ethyl propionate, methyl valerate and ethyl valerate), $C_1$–$C_6$ nitrogen-containing organic compounds (e.g., methylamine, dimethylamine, trimethylamine, ethylamine, diethylamine, triethylamine, aniline, pyridine, nitromethane and nitroethane), $C_1$–$C_4$ sulfur-containing organic compounds (e.g., methyl mercaptan, thiophene, dimethyl thioether and diethyl thioether); and inorganic compounds, such as hydrogen, ammonia, carbon monoxide, hydrogen sulfide, and carbon disulfide. Of these compounds, preferred are propane, isobutane, propylene, isobutene, methanol, ethanol, propanol, hydrogen, ammonia and carbon monoxide. More preferred are propane, isobutane, propylene, isobutene and ammonia. Especially preferred is ammonia. These compounds can be used individually or in combination.

In the process of the present invention, with respect to the amount of the combustible gas supplied into the fluidized-bed reactor during the course of the temperature elevation when the temperature of the catalyst composition (hereinafter, frequently referred to simply as "catalyst temperature") is 300° C. or higher, there is no particular limitation as long as the effects of the present invention can be achieved and the composition of a gaseous mixture effluent from an outlet of the reactor is maintained outside of an explosion range as measured at the outlet. However, the lower limit of the amount of the combustible gas is generally in the range of 0.1% by volume or more, preferably 0.5% by volume or more, more preferably 1.0% by volume or more, based on the total volume of the molecular oxygen-containing gas and the combustible gas both supplied into the reactor during the course of the temperature elevation when the catalyst temperature is 300° C. or higher. With respect to the selection of the upper limit of the amount of the combustible gas, it is desirable to take into consideration an economical disadvantage caused by the use of too large an amount of the combustible gas. Therefore, the upper limit of the amount of the combustible gas is generally in the range of 30% by volume or less, preferably 25% by volume or less, more preferably 20% by volume or less, based on the total volume of the molecular oxygen-containing gas and the combustible gas both supplied into the reactor during the course of the temperature elevation when the catalyst temperature is 300° C. or higher.

Elucidation has not yet been made with respect to the reason why, in the process of the present invention, a deterioration of the catalytic activity of the catalyst, which occurs by contact of the catalyst with a molecular oxygen-containing gas supplied during the temperature elevation, can be prevented by supplying a combustible gas, together with the molecular oxygen-containing gas, into the reactor during the course of the temperature elevation when the catalyst temperature is 300° C. or higher. However, it is considered that during the course of the temperature elevation when the catalyst temperature is 300° C. or higher, the combustible gas is adsorbed on the surface of the catalyst and the adsorbed combustible gas reacts with the molecular oxygen of the molecular oxygen-containing gas, thereby preventing the catalyst from undergoing oxidative deterioration before the start of the ammoxidation reaction. Further, with respect to the reason why such unexpected excellent effects of the present invention for preventing the deterioration of the catalytic activity can be exhibited even when only a small amount of the combustible gas is supplied into the reactor, the reason is believed to be as follows. In a fluidized-bed reactor, the catalyst particles are freely moved in the vertical and horizontal directions. Therefore, even if the amount of the combustible gas supplied into the reactor is small, the combustible gas is smoothly, uniformly dispersed in the fluidized catalyst bed, so that the entire of the catalyst is effectively contacted with the combustible gas.

In the process of the present invention, the supply of a combustible gas may be started at the catalyst temperature of 300° C. or higher, preferably between 300 and 380° C.

Examples of manners of supplying a combustible gas into the reactor in the process of the present invention include a method in which the combustible gas is supplied into the reactor in the form of a mixture thereof with the molecular oxygen-containing gas, and a method in which the combustible gas and the molecular oxygen-containing gas are separately supplied into the reactor through separate supply lines therefor.

The term "oxygen-containing gas" used herein means a mixture of molecular oxygen and a gas which is inert to the combustion reaction of a combustible gas.

Examples of molecular oxygen-containing gases supplied into the reactor during the course of the temperature elevation include air; a gaseous mixture obtained by diluting air with inert gas, such as nitrogen, argon, steam and carbon dioxide, so as to lower the oxygen concentration of the air; a gaseous mixture obtained by adding oxygen to air so as to increase the oxygen concentration of the air; a gas obtained by increasing the nitrogen or oxygen concentration of air by membrane separation or pressure swing adsorption (PSA); and pure oxygen gas. Among these molecular oxygen-containing gases, from an economical point of view, air can be most advantageously used.

In the process of the present invention, the ammoxidation reaction temperature is generally in the range of from 380 to 500° C., preferably from 400 to 470° C. The ammoxidation reaction pressure may generally be in the range of from atmospheric pressure to 3 atm. The time of contact (contact time) between gaseous feedstocks (i.e., propane or isobutane, ammonia and molecular oxygen) and the catalyst composition may generally be from 0.1 to 20 (sec·g/cc), preferably from 0.5 to 10 (sec·g/cc). In the process of the present invention, the contact time during the ammoxidation reaction of propane or isobutane is determined according to the following formula:

$$\text{Contact time (sec} \cdot \text{g/cc)} = (W/F) \times \frac{273}{(273+T)} \times \frac{(1.03+P)}{1.03}$$

wherein:

W represents the weight (g) of the catalyst composition contained in the fluidized-bed reactor;

F represents the flow rate (cc/sec) of the gaseous feedstocks [in terms of the value under the normal temperature and pressure conditions (0° C., 1 atm)];

T represents the ammoxidation reaction temperature (°C.); and

P represents the ammoxidation reaction pressure (kg/cm$^2$·G).

The linear velocity (LV) of the gaseous feedstocks fed into the fluidized-bed reactor is generally from 0.5 to 200 (cm/sec), preferably from 1 to 100 (cm/sec). In the present invention, the linear velocity (LV) is determined according to the following formula:

$$\text{Linear Velocity (cm/sec)} = F \times \frac{(273+T)}{273} \times \frac{1.03}{(1.03+P)} \times \frac{1}{S}$$

wherein:

S represents the horizontal inner cross-sectional area (cm$^2$) of a cylindrical fluidized-bed reactor; and F, T and P are as defined above.

In the process of the present invention, when the temperature of the catalyst composition reaches the ammoxidation reaction temperature, the supply of the combustible gas and the molecular oxygen-containing gas into the fluidized-bed reactor is changed to a feeding of propane or isobutane, ammonia and molecular oxygen (gaseous feedstocks) into the fluidized-bed reactor (that is, a transformation of a gas composition from the composition for the temperature elevation to the composition for the ammoxidation reaction is effected), to thereby effect an ammoxidation reaction of the propane or isobutane, thus producing acrylonitrile or methacrylonitrile. When the combustible gas used in the temperature elevation is comprised of one member selected from ammonia, propane, isobutane, a combination of ammonia and propane and a combination of ammonia and isobutane, the ammoxidation reaction of propane or isobutane can be started by, for example, a method in which, after the catalyst temperature has almost reached a predetermined ammoxidation reaction temperature, the composition of the molecular oxygen-containing gas (further containing a combustible gas), which is supplied into the reactor during the course of the temperature elevation when the catalyst temperature is 300° C. or higher, is gradually changed (transformed) to a composition of gaseous feedstocks which is suitable for the ammoxidation reaction, while also gradually changing the conditions in the reactor to ammoxidation conditions, namely, conditions which fall within the above-mentioned ranges with respect to the temperature, pressure, contact time, linear velocity of gaseous feedstocks and catalyst amount. On the other hand, when the combustible gas used in the temperature elevation is other than ammonia, propane, isobutane or a combination of ammonia and propane (or isobutane), the ammoxidation reaction of propane or isobutane can be started by, for example, a method in which, after the catalyst temperature has almost reached a predetermined ammoxidation reaction temperature, the amount of the combustible gas supplied into the reactor is gradually decreased while starting the feeding of and gradually increasing the amounts of ammonia and propane or isobutane so that the composition of the gases entering the reactor is gradually changed (transformed) to a suitable composition of gaseous feedstocks for the ammoxidation reaction, and while also gradually changing the conditions in the reactor to ammoxidation reaction conditions, namely conditions which fall within the above-mentioned ranges with respect to the temperature, pressure, contact time, linear velocity of gaseous feedstocks and catalyst amount.

With respect to the manner of the supplying each of the molecular oxygen-containing gas and the combustible gas during the course of the temperature elevation when the temperature of the catalyst composition is 300° C. or higher, there is no particular limitation, and each of these gases can be supplied either continuously or intermittently. That is, the supply of any of these gases may be temporarily stopped. However, it is preferred that both of the molecular oxygen-containing gas and the combustible gas are continuously supplied into the reactor.

With respect to the change-starting temperature (transformation threshold temperature) at which it is started to make a change from the supply of the molecular oxygen-containing gas in combination with the combustible gas into the reactor to a feeding of gaseous feedstocks for the ammoxidation reaction, there is no particular limitation. However, it is preferred that the above change-starting temperature is the ammoxidation reaction temperature, or that the above change-starting temperature is a temperature in the range of ±50° C., more advantageously ±30° C., relative to the ammoxidation reaction temperature.

The term "ammoxidation reaction of propane or isobutane" used in the present invention means a reaction of propane or isobutane with ammonia and molecular oxygen under substantially constant reaction conditions, so that acrylonitrile or methacrylonitrile is steadily produced.

A specific example of the process of the present invention is explained hereinbelow, referring to FIG. 1 of the accompanying drawing, which diagrammatically shows an example of a fluidized-bed reactor suitably employable when the process of the present invention is practiced for commercial-scale production of acrylonitrile or methacrylonitrile. In the example of the process of the present invention described below, ammonia is used as the combustible gas, and ammoxidation of propane is conducted.

First, a catalyst composition is charged into a fluidized-bed reactor. Air is externally heated by means of a heat exchanger utilizing heat generated by the combustion of a hydrocarbon fuel, and the resultant heated air is continuously supplied into a lower portion of the fluidized-bed reactor through line 1 for introducing air, in the direction indicated by the arrow depicted along line 1 in FIG. 1 and through a perforated bottom plate at the forward end of line 1, thereby providing fluidized catalyst bed 3 and also elevating the temperature of catalyst bed 3 from room temperature to 300° C. or higher. (The manner of preheating the catalyst bed to 300° C. or higher is not limited to the above manner, but various other manners can be mentioned, for example, preheating of the catalyst composition outside of the reactor and transferring of the preheated catalyst composition into the reactor, preheating of the catalyst composition in an atmosphere of inert gas, and the like.) The air in the reactor is discharged through outlet 4 and line 5 in the direction indicated by the arrow depicted along line 5 in FIG. 1. Then, simultaneously with the supply of air into the reactor through line 1, ammonia is continuously supplied into a lower portion of the reactor through line 2, in the direction indicated by the arrow depicted along line 2 in FIG. 1, and through a sparger (which is positioned at the forward end portion of line 2), and the catalyst temperature is further elevated by the heat of combustion due to the combustion reaction of the ammonia ($NH_3 + 3/4 O_2 \rightarrow 1/2 N_2 + 3/2 H_2O$). During the course of the temperature elevation, the amount of ammonia being supplied into the reactor is gradually increased until the amount of ammonia being supplied becomes 10 to 20% by volume, based on the total volume of air and ammonia both being supplied into the reactor, and the catalyst temperature is adjusted to about 430° C. After the catalyst temperature has reached about 430° C., the feeding of propane into the reactor is started while continuing to feed ammonia and air into the reactor for the ammoxidation reaction, and propane is fed through line 2 in the direction indicated by the arrow depicted along line 2 in FIG. 1, and the amount of propane fed is gradually increased while adjusting the proportions of propane, ammonia and air to a value within a range suitable for the ammoxidation reaction. At the same time, the conditions in the reactor are gradually changed toward ammoxidation reaction conditions which fall within appropriate predetermined ranges of temperature, pressure, contact time, linear velocity of gaseous feedstocks and catalyst amount. In this manner, the ammoxidation reaction of propane can be conducted in a steady state. The produced acrylonitrile flows out of the reactor through outlet 4 and line 5 in the direction indicated by the arrow depicted along line 5 in FIG. 1. (During the temperature elevation and the ammoxidation reaction, the composition of a gaseous mixture effluent from outlet 4 of the reactor is controlled so as to be maintained outside of an explosion range.)

After termination of the ammoxidation reaction, the catalyst temperature in the fluidized-bed reactor may be lowered. During the lowering of the catalyst temperature, when the catalyst at 300° C. or higher is contacted with molecular oxygen, the catalyst is likely to be deteriorated. However, this deterioration of the catalyst can be prevented by supplying into the reactor a combustible gas (as defined above) together with a molecular oxygen-containing gas during the course of the temperature lowering when the catalyst temperature is 300° C. or higher.

The catalyst composition used in the process of the present invention contains an oxide catalyst comprising a compound oxide of molybdenum, vanadium, niobium and at least one element selected from tellurium and antimony.

Specific examples of compound oxides include a compound oxide represented by the following formula (1):

$$Mo_{1.0}V_aNb_bA_cO_x \tag{1}$$

wherein:

A is at least one element selected from the group consisting of tellurium and antimony;
and a, b, c and x are, respectively, the atomic ratios of vanadium, niobium, A and oxygen, relative to the molybdenum, wherein a is a number from 0.01 to 1.0, preferably from 0.1 to 0.5;

b is a number from 0.01 to 1.0, preferably from 0.05 to 0.5;

c is a number from 0.01 to 1.0, preferably from 0.05 to 0.5; and x is a number determined by the valence requirements of the other elements present.

The oxide catalyst contained in the catalyst composition used in the process of the present invention may further contain, in an atomic ratio of 0.3 or less relative to one atom of the molybdenum, at least one element selected from tantalum, tungsten, titanium, zirconium, hafnium, iron, chromium, manganese, rhenium, ruthenium, cobalt, rhodium, nickel, palladium, osmium, iridium, platinum, copper, silver, zinc, cadmium, boron, aluminum, gallium, indium, thallium, germanium, tin, lead, phosphorus, bismuth, selenium, scandium, yttrium, lanthanum, cerium, praseodymium, neodymium, samarium, gadolinium, alkali metals and alkaline earth metals.

The catalyst composition used in the process of the present invention comprises a carrier having supported thereon an oxide catalyst. Examples of carriers used in the present invention include silica, alumina, silica-alumina, magnesia, titania and zirconia. Among these carriers, preferred is silica. These carriers can be used individually or in the form of a composite thereof.

With respect to the catalyst composition used in the present invention, the carrier is preferably present in an amount of from 10 to 70% by weight, more preferably 20 to 60% by weight, based on the total weight of the carrier and the oxide catalyst.

With respect to the form of the source of each component element for the catalyst used in the process of the present invention, there is no particular limitation as long as the source contains a desired element. Representative examples of sources of component elements for the catalyst composition used in the present invention include ammonium paramolybdate $[(NH_4)_6Mo_7O_{24}\cdot 4H_2O]$ as a source of molybdenum; ammonium metavanadate ($NH_4VO_3$) as a source of vanadium; niobium hydrogenoxalate $[Nb(HC_2O_4)_5 \cdot nH_2O]$ and niobic acid ($Nb_2O_5 \cdot nH_2O$) as a source of niobium; telluric acid ($H_6TeO_6$) as a source of tellurium; and antimony trioxide ($Sb_2O_3$) as a source of antimony.

Further examples of sources of component elements for the catalyst include oxides, ammonium salts, nitrates, chlorides, sulfates and organic acid salts of desired elements.

With respect to the source of a component element for the carrier used in the catalyst composition, there is no particular limitation as long as the source contains a desired element for the carrier. Examples of sources of component elements for the carrier include oxides, hydroxides, inorganic salts and organic salts of desired elements. Further, a source in the form of a sol or a gel can also be used.

The catalyst composition used in the process of the present invention can be produced, for example, as follows.

A slurry of raw materials for the catalyst composition used in the present invention can be prepared, for example, as follows: sources of elements, such as molybdenum, vanadium and tellurium, are dissolved in water or an aqueous solution of nitric acid, and a source of a component element for the carrier is added to the resultant solution, followed by further addition of a solution of a source of niobium, to thereby obtain a slurry. Further, with respect to antimony and vanadium, a slurry or solution containing antimony and vanadium, which is obtained by adding antimony oxide to an aqueous solution of ammonium metavanadate, followed by heat treatment under reflux conditions, can also be suitably used. In the preparation of the slurry, the order of mixing together solutions of raw materials can be arbitrarily changed.

The above-mentioned slurry of raw materials can be dried by subjecting it to spray drying to thereby obtain a dried catalyst composition precursor in the form of a spherical particulate powder.

The dried catalyst composition precursor obtained in the above-mentioned manner is subjected to calcination in an atmosphere of inert gas, such as gaseous nitrogen, argon and helium, which is substantially free of molecular oxygen, at a temperature of 450 to 800° C., preferably 500 to 700° C. for 1 to 20 hours, thereby obtaining a catalyst composition comprising a carrier having supported thereon an oxide catalyst comprising a compound oxide.

With respect to the inert gas for use in the calcination, which is substantially free of molecular oxygen, the concentration of molecular oxygen in the inert gas is preferably 800 ppm or less, more preferably 500 ppm or less, especially preferably 200 ppm or less.

The dried catalyst composition precursor obtained in the above-mentioned manner may be heat-treated in an atmosphere of air at a temperature of 150 to 450° C. before the calcination.

For the heat-treatment and calcination, use can be made of a kiln, such as a rotary kiln, a tunnel kiln, a muffle kiln and a fluidized firing kiln, in which the conditions of the internal atmosphere can be controlled.

Thus, a catalyst composition, which has excellent fluidity and abrasion resistance and therefore can be suitably used for a fluidized bed reaction, can be obtained.

With respect to the gaseous feedstock used for the ammoxidation reaction in the process of the present invention, propane or isobutane can be used, and propane is especially preferred. Ammonia used in the process of the present invention need not be of a very high purity but may be of a commercial grade.

In the process of the present invention, as a source of molecular oxygen, air is generally preferred from an economical view point. A further example of a source of molecular oxygen is a gaseous mixture obtained by, for example, adding molecular oxygen to air so as to increase the oxygen concentration of the air. Gaseous feedstocks for the ammoxidation reaction may be diluted with inert gas (such as helium, argon, nitrogen or carbon dioxide), steam or the like.

The molar ratio of each of ammonia and molecular oxygen to propane or isobutane used for the ammoxidation reaction can be appropriately selected in accordance with the type of the reaction mode used, such as a one-pass mode and a recycling mode. For example, when the ammoxidation reaction is conducted by a one-pass mode, for increasing the conversion of the propane or isobutane, the molar ratio of ammonia to propane or isobutane is generally 0.8 to 4, preferably 1 to 3, and the molar ratio of molecular oxygen to propane or isobutane is generally 0.5 to 6, preferably 1 to 4. Further, when unreacted propane or isobutane in the ammoxidation reaction is recycled (i.e., when a recycling mode is used), for increasing the selectivity for a desired unsaturated nitrile namely, acrylonitrile or methacrylonitrile, it is preferred that the reaction is conducted under conditions wherein the conversion of propane or isobutane is suppressed to a level as low as possible. Therefore, when a recycling mode is used, the molar ratio of ammonia to propane or isobutane is generally 0.1 to 1, preferably 0.2 to 0.8, and the molar ratio of molecular oxygen to propane or isobutane is generally 0.1 to 4, preferably 0.2 to 2.

With respect to propane or isobutane used in the process of the present invention, the propane or isobutane may be mixed into ammonia and a molecular oxygen-containing gas, and then the resultant gaseous feed-stock mixture can be fed into the reactor. Further, propane or isobutane may first be mixed with ammonia to obtain a gaseous mixture of propane or isobutane and ammonia, and then the obtained gaseous mixture and a molecular oxygen-containing gas can be individually, separately fed into the reactor so as to allow them to be mixed and contacted with each other. Further, propane or isobutane, ammonia and a molecular oxygen-containing gas may be individually, separately fed into the reactor so as to allow them to be mixed and contacted with each other in the reactor. Still further, each of ammonia and a molecular oxygen-containing gas may be fed into the reactor in a stepwise manner.

BEST MODE FOR CARRYING OUT THE INVENTION

Hereinbelow, the present invention will be described in more detail with reference to the following Examples and Comparative Examples as well as Reference Example, which should not be construed as limiting the scope of the present invention.

In the following Examples and Comparative Examples, the conversion (%) of propane and the yield (%) of acrylonitrile, both used for evaluating the results of the ammoxidation reaction of propane, are defined as follows:

$$\text{Conversion (\%) of propane} = \frac{(\text{mole of propane consumed})}{(\text{mole of propane fed})} \times 100$$

$$\text{Yield (\%) of acrylonitrile} = \frac{(\text{mole of acrylonitrile formed})}{(\text{mole of propane fed})} \times 100$$

REFERENCE EXAMPLE (Preparation of a catalyst composition)

A catalyst composition comprising a silica carrier having supported thereon an oxide catalyst, wherein the silica carrier is present in an amount of 30% by weight, based on the total weight of the silica carrier and the oxide catalyst, and wherein the oxide catalyst comprises a compound oxide represented by the formula: $Mo_{1.0}V_{0.33}Nb_{0.11}Te_{0.22}O_x$, was prepared as follows.

356.7 g of ammonium metavanadate ($NH_4VO_3$) was dissolved in 7,200 g of water at a temperature of about 60° C. while stirring. To the resultant solution were successively added 467.7 g of telluric acid ($H_6TeO_6$) and 1,632.0 g of ammonium paramolybdate [$(NH_4)_6Mo_7O_{24} \cdot 4H_2O$], to thereby obtain a solution. To the obtained solution was added 3,000 g of silica sol having a $SiO_2$ content of 30 wt %, followed by addition of a niobium-containing solution (which was prepared by a method in which 345.6 g of 25 wt % aqueous ammonia and 1,336.5 g of water were mixed to each other and 834.7 g of niobium hydrogenoxalate [$Nb(HC_2O_4)_5 \cdot nH_2O$] ($Nb_2O_5$ content: 16.2% by weight) was dissolved in the resultant solution), to thereby obtain a slurry. The obtained slurry was subjected to spray drying at a temperature of about 200° C. to obtain a dried particulate catalyst composition precursor. The obtained catalyst composition precursor was heat-treated by means of an electric kiln in an atmosphere of air at 275° C. for 2 hours, and then subjected to calcination at 600° C. for 2 hours under a stream of nitrogen gas having an oxygen concentration of only 1 ppm, to thereby obtain a catalyst composition.

Example 1

Using the catalyst composition obtained in the Reference Example above, an ammoxidation reaction of propane was conducted as follows.

30 g of the obtained catalyst composition was charged into a Vycor glass fluidized-bed reactor having an inner diameter of 25 mm. The fluidized-bed reactor containing the catalyst composition was placed in an electric furnace. The temperature of the catalyst composition in the reactor was elevated from room temperature to 300° C. over 2 hours while supplying air into the fluidized-bed reactor at a flow rate of 8.65 Ncc/sec (Ncc means cc as measured under the normal temperature and pressure conditions, namely at 0° C. under 1 atm.). Then, the temperature of the catalyst composition was further elevated from 300° C. to 430° C. over 2 hours while supplying a gaseous mixture of air and ammonia having an ammonia content of 2% by volume into the reactor at a flow rate of 8.65 Ncc/sec. At a point in time when the temperature of the catalyst composition reached 430° C., the concentration of oxygen in the gaseous mixture effluent from the outlet of the reactor (hereinafter, frequently referred to simply as "oxygen concentration at the reactor outlet") was about 18% by volume.

Then, the supply of air and ammonia into the fluidized-bed reactor was stepwise changed to a feeding of gaseous feedstocks of propane, ammonia and air wherein the [propane: ammonia: air] volume ratio is 1.0:1.0:13.0. The stepwise change of the composition of a gaseous mixture in the reactor to a composition suitable for the ammoxidation reaction was performed by changing the gas in the reactor ten times by a ¹⁄₁₀ volume of the entire volume at each time at intervals of about 10 minutes. Finally, the gaseous feedstocks were fed into the reactor at a flow rate of 8.65 Ncc/sec, to thereby effect an ammoxidation reaction of propane to produce acrylonitrile.

During the ammoxidation reaction of propane, the reaction temperature was maintained at 430° C., the reaction pressure was maintained at 0.5 kg/cm²·G and the contact time between the catalyst composition and the gaseous feedstocks was maintained at 2.0 sec·g/cc.

The results of the ammoxidation reaction were evaluated in terms of the conversion (%) of propane and the yield (%) of acrylonitrile as defined by the above formulae. As a result, it was found that the conversion of propane and the yield of acrylonitrile were 72.2% and 44.0%, respectively.

The results of the above ammoxidation reaction are shown in Table 1.

Comparative Example 1

Substantially the same procedure as in Example 1 was repeated, except that the temperature of the catalyst composition in the fluidized-bed reactor was gradually elevated from room temperature to 430° C. over 4 hours while supplying air into the fluidized-bed reactor at a flow rate of 8.65 Ncc/sec. At a point in time when the temperature of the catalyst composition reached 430° C., the oxygen concentration at the reactor outlet was about 21% by volume.

The results of the ammoxidation were evaluated in terms of the conversion (%) of propane and the yield (%) of acrylonitrile as defined by the above formulae. As a result, it was found that the conversion of propane and the yield of acrylonitrile were 60.0% and 31.2%, respectively.

The results of the above ammoxidation reaction are shown in Table 1.

Example 2

The temperature elevation of the catalyst composition in the fluidized-bed reactor was conducted in substantially the same manner as in Example 1 except that, instead of the gaseous mixture of air and ammonia having an ammonia content of 2% by volume in Example 1, a gaseous mixture of air and ammonia having an ammonia content 10% by volume is supplied into the reactor during the temperature elevation of the catalyst composition from 300° C. to 430° C. At a point in time when the temperature of the catalyst composition reached 430° C., the oxygen concentration at the reactor outlet was about 11% by volume.

Then, substantially the same procedure for ammoxidation reaction of propane as in Example 1 was repeated.

The results of the ammoxidation reaction were evaluated in terms of the conversion (%) of propane and the yield (%) of acrylonitrile as defined by the above formulae. As a result, it was found that the conversion of propane and the yield of acrylonitrile were 72.6% and 44.5%, respectively.

The results of the above ammoxidation reaction are shown in Table 1.

Comparative Example 2

The temperature elevation of the catalyst composition in the fluidized-bed reactor was conducted in substantially the same manner as in Example 1 except that, instead of the gaseous mixture of air and ammonia having an ammonia content of 2% by volume in Example 1, a gaseous mixture of nitrogen and air having an oxygen concentration of 11% by volume was supplied into the reactor during the temperature elevation of the catalyst-composition from 300° C. to 430° C. At a point in time when the temperature of the catalyst composition reached 430° C., the oxygen concentration at the reactor outlet was about 11% by volume.

Then, substantially the same procedure for ammoxidation reaction of propane as in Example 1 was repeated.

The results of the ammoxidation reaction were evaluated in terms of the conversion (%) of propane and the yield (%) of acrylonitrile as defined by the above formulae. As a result, it was found that the conversion of propane and the yield of acrylonitrile were 61.8% and 34.5%, respectively.

The results of the above ammoxidation reaction are shown in Table 1.

Example 3

The temperature elevation of the catalyst composition in the fluidized-bed reactor was conducted in substantially the same manner as in Example 1 except that, instead of the gaseous mixture of air and ammonia having an ammonia content of 2% by volume in Example 1, a gaseous mixture of air and propane having a propane content of 1% by volume was supplied into the reactor during the temperature elevation of the catalyst composition from 300° C. to 430°

C. At a point in time when the temperature of the catalyst composition reached 430° C., the oxygen concentration at the reactor outlet was about 17% by volume.

Then, substantially the same procedure for ammoxidation reaction of propane as in Example 1 was repeated.

The results of the ammoxidation reaction were evaluated in terms of the conversion (%) of propane and the yield (%) of acrylonitrile as defined by the above formulae. As a result, it was found that the conversion of propane and the yield of acrylonitrile were 70.6% and 41.0%, respectively.

The results of the above ammoxidation reaction are shown in Table 1.

Example 4

The temperature elevation of the catalyst composition in the fluidized-bed reactor was conducted in substantially the same manner as in Example 1 except that, instead of the gaseous mixture of air and ammonia having an ammonia content of 2% by volume in Example 1, a gaseous mixture of air and propylene having a propylene content of 3.5% by volume was supplied into the reactor during the temperature elevation of the catalyst composition from 300° C. to 430° C. At a point in time when the temperature of the catalyst composition reached 430° C., the oxygen concentration at the reactor outlet was about 8% by volume.

Then, substantially the same procedure for ammoxidation reaction of propane as in Example 1 was repeated.

The results of the ammoxidation reaction were evaluated in terms of the conversion (%) of propane and the yield (%) of acrylonitrile as defined by the above formulae. As a result, it was found that the conversion of propane and the yield of acrylonitrile were 72.8% and 44.2%, respectively.

The results of the above ammoxidation reaction are shown in Table 1.

Example 5

Using the catalyst composition obtained in Reference Example above, an ammoxidation reaction of propane was conducted as follows.

1,000 g of the obtained catalyst composition was charged into a stainless steel (SUS304) fluidized-bed reactor having an outer diameter of 3 inches. The fluidized-bed reactor containing the catalyst composition was placed in an electric furnace. The temperature of the catalyst composition in the reactor was elevated from room temperature to 300° C. over 2 hours under a pressure of 0.5 kg/cm$^2$·G while supplying air into the fluidized-bed reactor from the bottom thereof at a flow rate of 200 Ncc/sec. Then, the temperature of the catalyst composition was further elevated from 300° C. to 430° C. over 2 hours while supplying ammonia into the reactor through a nozzle located 2 cm above the bottom of the reactor, wherein the flow rate of the ammonia was initially 2.78 Ncc/sec and was increased by 2.78 Ncc/sec per about 10 minutes while maintaining the total flow rate of the gases supplied into the reactor at 200 Ncc/sec. At a point in time when the temperature of the catalyst composition reached 430° C., the oxygen concentration at the reactor outlet was about 6% by volume.

Then, the supply of air and ammonia into the fluidized-bed reactor was stepwise changed to a feeding of gaseous feedstocks of propane, ammonia and air into the reactor, wherein the propane and ammonia are fed through a nozzle located 2 cm above the bottom of the reactor, whereas the air is fed from the bottom of the reactor, and wherein the [propane: ammonia: air] volume ratio is 1.0:1.05:13.0. The stepwise change of the composition of a gaseous mixture in the reactor to a composition suitable for the ammoxidation reaction was performed by changing the gas in the reactor ten times by a 1/10 volume of the entire volume at each time at intervals of about 20 minutes. Finally, the gaseous feedstocks were fed into the reactor at a flow rate of 200 Ncc/sec, to thereby effect an ammoxidation reaction of propane to produce acrylonitrile.

The results of the ammoxidation reaction were evaluated in terms of the conversion (%) of propane and the yield (%) of acrylonitrile as defined by the above formulae. As a result, it was found that the conversion of propane and the yield of acrylonitrile were 75.6% and 45.0%, respectively.

The results of the above ammoxidation reaction are shown in Table 1.

Comparative Example 3

The temperature elevation of the catalyst composition in the fluidized-bed reactor was conducted in substantially the same manner as in Example 5 except that the temperature of the catalyst composition in the reactor was elevated from room temperature to 430° C. over 4 hours while supplying air into the reactor. At a point in time when the temperature of the catalyst composition reached 430° C., the oxygen concentration at the reactor outlet was about 21% by volume.

Then, substantially the same procedure for ammoxidation reaction of propane as in Example 5 was repeated.

The results of the ammoxidation reaction were evaluated in terms of the conversion (%) of propane and the yield (%) of acrylonitrile as defined by the above formulae. As a result, it was found that the conversion of propane and the yield of acrylonitrile were 65.0% and 32.5%, respectively.

The results of the above ammoxidation reaction are shown in Table 1.

Comparative Example 4

A catalyst composition comprising a silica carrier having supported thereon an oxide catalyst, wherein the silica carrier is present in an amount of 30% by weight, based on the total weight of the silica carrier and the oxide catalyst and wherein the oxide catalyst comprises a compound oxide described in Working Example 6 of U.S. Pat. No. 5,334,743 and represented by the formula: $Mn_{0.4}V_{0.05}Mo_{0.4}O_{1.75}$, was prepared as follows.

546.3 g of ammonium paramolybdate [$(NH_4)_6Mo_7O_{24}\cdot 4H_2O$] and 45.7 g of ammonium metavanadate ($NH_4VO_3$) were dissolved in 1,100.2 g of water. To the resultant solution was added 1,000 g of silica sol having a $SiO_2$ content of 30 wt %, followed by addition of a manganese-containing solution which was prepared by dissolving 897.1 g of manganese nitrate [$Mn(NO_3)_2\cdot 6H_2O$] in 410.0 g of 16.6 wt % nitric acid, to thereby obtain a slurry. The obtained-slurry was subjected to spray drying at a temperature of 200° C., to obtain a dried particulate catalyst composition precursor. The obtained catalyst composition precursor was heat-treated by means of an electric kiln in an atmosphere of air at 300° C. for 2 hours, and then subjected to calcination in an atmosphere of air at 500° C. for 4 hours, to thereby obtain a catalyst composition.

Using the catalyst composition obtained above, an ammoxidation reaction of propane was conducted as follows.

Substantially the same temperature elevation operation as in Example 1 was repeated except that, instead of the catalyst composition used in Example 1, the catalyst composition obtained above was used, and that, instead of the final elevation temperature (430° C.) used in Example 1, the temperature of the catalyst composition was elevated to 450°

C. At a point in time when the temperature of the catalyst composition reached 450° C., the oxygen concentration at the reactor outlet was about 18% by volume.

Then, an ammoxidation reaction of propane was conducted in substantially the same manner as in Example 1 except that the ammoxidation reaction temperature was 450° C. instead of 430° C., the contact time between the catalyst composition and the gaseous feedstocks was 1.9 sec·g/cc (instead of 2.0 sec·g/cc) and the [propane: ammonia: air] volume ratio was 1.0:1.0:11.3 (instead of 1.0:1.0:13.0).

The results of the ammoxidation reaction were evaluated in terms of the conversion (%) of propane and the yield (%) of acrylonitrile as defined by the above formulae. As a result, it was found that the conversion of propane and the yield of acrylonitrile were 22.5% and 0.6%, respectively.

The results of the above ammoxidation reaction are shown in Table 1.

Comparative Example 5

Using the catalyst composition obtained in Comparative Example 4, an ammoxidation reaction of propane was conducted as follows.

Substantially the same temperature elevation operation as in Comparative Example 1 was repeated except that, instead of the catalyst composition used in Comparative Example 1, the catalyst composition obtained in Comparative Example 4 was used, and that, instead of the final elevation temperature (430° C.) used in Comparative Example 1, the temperature of the catalyst composition was elevated to 450° C. At a point in time when the temperature of the catalyst composition reached 450° C., the oxygen concentration at the reactor outlet was about 21% by volume.

Then, substantially the same procedure for ammoxidation reaction of propane as in Comparative Example 4 was repeated.

The results of the ammoxidation reaction were evaluated in terms of the conversion (%) of propane and the yield (%) of acrylonitrile as defined by the above formulae. As a result, it was found that the conversion of propane and the yield of acrylonitrile were 22.3% and 0.6%, respectively.

The results of the above ammoxidation reaction are shown in Table 1.

TABLE 1

| Examples and Comparative Examples | Type of the gas(es) supplied into the reactor during the temperature elevation from 300°0 C. to 430° C. | Oxygen concentration at the reactor outlet at 430° C. (% by volume) | [Propane/ammonia/ air] volume ratio | Conversion of propane (%) | Yield of acrylonitrile (%) |
|---|---|---|---|---|---|
| Example 1 | air + ammonia (ammonia content: 2% by volume) | about 18 | 1.0/1.0/13.0 | 72.2 | 44.0 |
| Example 2 | air + ammonia (ammonia content:- 10% by volume) | about 11 | 1.0/1.0/13.0 | 72.6 | 44.5 |
| Example 3 | air + propane (propane content: 1% by volume) | about 17 | 1.0/1.0/13.0 | 70.6 | 41.0 |
| Example 4 | air + propylene (propylene content: 3.5% by volume) | about 8 | 1.0/1.0/13.0 | 72.8 | 44.2 |
| Example 5 | air + ammonia[1] | about 6 | 1.0/1.05/13.0 | 75.6 | 45.0 |
| Comparative Example 1 | air | about 21 | 1.0/1.0/13.0 | 60.0 | 31.2 |
| Comparative Example 2 | air + nitrogen (oxygen concentration: 11% by volume) | about 11 | 1.0/1.0/13.0 | 61.8 | 34.5 |
| Comparative Example 3 | air | about 21 | 1.0/1.05/13.0 | 65.0 | 32.5 |
| Comparative Example 4 | air + ammonia[2] (ammonia content: 2% by volume) | about 18[3] | 1.0/1.0/11.3 | 22.5 | 0.6 |
| Comparative Example 5 | air[2] | about 21[3] | 1.0/1.0/11.3 | 22.3 | 0.6 |

Note [1]While maintaining the total flow rate of the gases supplied into the reactor at 200 Ncc/sec, the flow rate of ammonia was increased by 2.78 Ncc/sec per about 10 minutes.
Note [2]Supplied into the reactor during the temperature elevation from 300° C. to 450° C.
Note [3]Measured at a temperature of 450° C.

INDUSTRIAL APPLICABILITY

In a process for producing acrylonitrile or methacrylonitrile by ammoxidation in the presence of a catalyst composition, by virtue of the unique operation for temperature elevation of the catalyst bed using both a molecular oxygen-containing gas and a combustible gas when the temperature of the catalyst composition is 300° C. or higher, the process of the present invention is advantageous in that the temperature elevation of a catalyst comprising a compound oxide of molybdenum, vanadium, niobium and at least one element selected from tellurium and antimony can be performed without suffering a deterioration of the catalytic activity of the catalyst during the temperature elevation of the catalyst, thereby allowing the catalyst to fully exhibit excellent performance thereof.

What is claimed is:

1. A process for producing acrylonitrile or methacrylonitrile from propane or isobutane by ammoxidation at a temperature in the range of from 380 to 500° C. (ammoxidation reaction temperature) in a fluidized-bed reactor containing a catalyst composition comprising a carrier having supported thereon an oxide catalyst, said oxide catalyst comprising a compound oxide of molybdenum, vanadium, niobium and at least one element selected from the group consisting of tellurium and antimony, said process comprising:
(1) providing a fluidized-bed reactor containing said catalyst composition preheated to a temperature of not lower than 300° C. and lower than said ammoxidation reaction temperature;
(2) elevating the temperature of said preheated catalyst composition in said fluidized-bed reactor, while supplying into said fluidized-bed reactor a molecular oxygen-containing gas together with a combustible gas capable of combustion by reaction with said molecular oxygen in the presence of said catalyst composition, until the temperature of the catalyst composition reaches said ammoxidation reaction temperature; and (3) changing the supply of the combustible gas and the molecular oxygen-containing gas into said fluidized-bed reactor to a feeding of propane or isobutane, ammonia and molecular oxygen into said fluidized-bed reactor when the temperature of the catalyst composition reaches said ammoxidation reaction temperature, to thereby effect an ammoxidation reaction of said propane or isobutane, thus producing acrylonitrile or methacrylonitrile.

2. The process according to claim 1, wherein said combustible gas is at least one compound selected from the group consisting of $C_1$–$C_8$ alkanes, $C_2$–$C_8$ alkenes, $C_2$–$C_4$ alkynes, $C_4$–$C_5$ dienes, $C_3$–$C_8$ cycloalkanes, $C_4$–$C_8$ cycloalkenes, $C_6$–$C_9$ aromatic hydrocarbons, $C_1$–$C_8$ alcohols, $C_2$–$C_7$ ethers, $C_1$–$C_3$ aldehydes, $C_2$–$C_3$ epoxides, $C_2$–$C_8$ ketones, $C_1$–$C_4$ nitrites, $C_1$–$C_4$ carboxylic acids, $C_2$–$C_5$ esters, $C_1$–$C_6$ nitrogen-containing organic compounds, $C_1$–$C_4$ sulfur-containing organic compounds, hydrogen, ammonia, carbon monoxide, hydrogen sulfide and carbon disulfide.

3. The process according to claim 1, wherein said combustible gas is at least one compound selected from the group consisting of propane, isobutane, propylene, isobutene, methanol, ethanol, propanol, hydrogen, ammonia and carbon monoxide.

4. The process according to claim 1, wherein said combustible gas is ammonia.

* * * * *

UNITED STATES PATENT AND TRADEMARK OFFICE
CERTIFICATE OF CORRECTION

PATENT NO. : 6,080,882
DATED : June 27, 2000
INVENTOR(S) : Hideo Midorikawa et al.

It is certified that error appears in the above-identified patent and that said Letters Patent is hereby corrected as shown below:

Column 22,
Line 3, delete "nitrites", and insert -- nitriles --.

Signed and Sealed this

Second Day of May, 2006

JON W. DUDAS
*Director of the United States Patent and Trademark Office*